(12) United States Patent
Bertin et al.

(10) Patent No.: US 11,253,633 B2
(45) Date of Patent: Feb. 22, 2022

(54) POROUS COMPOSITION FILLED WITH AN ACTIVE INGREDIENT

(71) Applicant: I.CERAM, Limoges (FR)

(72) Inventors: François Bertin, Limoges (FR); Eric Denes, Limoges (FR); Fabrice Fiorenza, Limoges (FR); Franck Sturtz, Limoges (FR); Daniel Setton, Limoges (FR)

(73) Assignee: I.CERAM, Limoges (FR)

( * ) Notice: Subject to any disclaimer, the term of this patent is extended or adjusted under 35 U.S.C. 154(b) by 87 days.

(21) Appl. No.: 15/521,779

(22) PCT Filed: Oct. 27, 2015

(86) PCT No.: PCT/EP2015/074910
§ 371 (c)(1),
(2) Date: Apr. 25, 2017

(87) PCT Pub. No.: WO2016/066660
PCT Pub. Date: May 6, 2016

(65) Prior Publication Data
US 2017/0232149 A1    Aug. 17, 2017

(30) Foreign Application Priority Data
Oct. 27, 2014 (FR) ..................................... 1460316

(51) Int. Cl.
| | | |
|---|---|---|
| *A61L 27/54* | (2006.01) | |
| *A61L 27/56* | (2006.01) | |
| *A61K 9/00* | (2006.01) | |
| *A61K 31/498* | (2006.01) | |
| *A61L 27/10* | (2006.01) | |
| *A61L 27/18* | (2006.01) | |

(52) U.S. Cl.
CPC ............ *A61L 27/54* (2013.01); *A61K 9/0024* (2013.01); *A61K 31/498* (2013.01); *A61L 27/105* (2013.01); *A61L 27/18* (2013.01); *A61L 27/56* (2013.01); *A61L 2300/406* (2013.01); *A61L 2300/416* (2013.01); *A61L 2430/02* (2013.01)

(58) Field of Classification Search
None
See application file for complete search history.

(56) References Cited

U.S. PATENT DOCUMENTS

| | | | |
|---|---|---|---|
| 4,192,021 A | 3/1980 | Deibig et al. | |
| 5,314,478 A | 5/1994 | Oka et al. | |
| 5,626,861 A | 5/1997 | Laurencin et al. | |
| 5,639,402 A * | 6/1997 | Barlow | A61F 2/28 264/6 |
| 6,417,247 B1 | 7/2002 | Armstrong et al. | |
| 6,989,033 B1 | 1/2006 | Schmidt | |
| 7,037,304 B2 | 5/2006 | Lyles et al. | |
| 2009/0311221 A1* | 12/2009 | Yudoh | A61L 27/26 424/93.7 |
| 2011/0117165 A1 | 5/2011 | Melican et al. | |
| 2011/0182965 A1* | 7/2011 | Mckay | A61F 2/4644 424/426 |
| 2012/0136456 A1* | 5/2012 | Better | C04B 35/48 623/23.51 |
| 2012/0172454 A1 | 7/2012 | Gaudriault | |
| 2017/0128622 A1* | 5/2017 | Spirio | A61L 27/227 |

FOREIGN PATENT DOCUMENTS

| | | | | |
|---|---|---|---|---|
| FR | 2823674 A1 * | 10/2002 | ............ | A61L 27/56 |
| JP | 10179713 | 7/1998 | | |

OTHER PUBLICATIONS

Machine translation, FR 2823674 (Year: 2002).*
Badilla et al., "Methods of Antibiotic Installation in Porous Orbital Implants", Ophthalmic Plastic & Reconstructive Surgery, 24(4), pp. 287-289, Abstract. (Year: 2008).*
Database WPI Section Ch Week 199837, Derwent Publications Ltd., London, GB; Class A96, AN 1998-431426, XP002741194, Kikutani T; Shibuya T: "Biologically active cement composition for bonding fixation of implant materials, supplementation filling of bone deficit part and artificial bones—consists of specific alumina powder, dimethacrylate group monomer, polymerisation initiator, promoter, retarder and osteogenesis factor".
Ikada Y et al.: "Release of antibiotic from composites of hydroxyapatite and poly(lactic acid)", Journal of Controlled Release, Elsevier, Amsterdam, NL, vol. 2, Nov. 1, 1985 (Nov. 1, 1985), pp. 179-186, XP025943002, ISSN: 0168-3659, [retrieved on Nov. 1, 1985], DOI: 10.1016/0168-3659(85)90043-4.
K. Al-Tahami; J. Singh: "Recent Patents on Drug Delivery & Formulation", vol. 1, 2007, Bentham Science Publishers, article "Smart Polymer Based Delivery Systems for Peptide and Proteins", pp. 65-71.

* cited by examiner

*Primary Examiner* — Bethany P Barham
*Assistant Examiner* — Barbara S Frazier
(74) *Attorney, Agent, or Firm* — Duane Morris LLP; Gregory M. Lefkowitz; Brandon A. Chan

(57) ABSTRACT

The invention relates to a composition for the release of an active ingredient, comprising a porous matrix, a filled carrier in the matrix and the active ingredient in the carrier. The invention is suitable for the treatment of bone cancers.

6 Claims, No Drawings

POROUS COMPOSITION FILLED WITH AN ACTIVE INGREDIENT

CROSS-REFERENCE TO RELATED APPLICATIONS

This application is a § 371 national stage entry of International Application No. PCT/EP2015/074910, filed Oct. 27, 2015, which claims priority to French Patent Application No. 1460316, filed Oct. 27, 2014, the entire contents of which is incorporated herein by reference.

TECHNICAL FIELD OF THE INVENTION

The invention relates to a composition for releasing an active principle, comprising a porous matrix, particularly made of ceramic, loaded with a carrier comprising an active principle.

TECHNICAL BACKGROUND

When performing surgery to treat bone cancer, whether primary or secondary, and particularly for treatment of bone metastases, or in the event of bone infection, the surgeon is led to remove the sick/infected part of the bone. It is therefore sometimes necessary to replace same. A plurality of techniques exist for this purpose (e.g. amputation, major excision around the tumour, use of a prosthesis and Illizaroff-type lengthening system), but said techniques all present a major problem, namely the occurrence of infection.

There is therefore a need to make a prosthesis or implant available that does not present the aforementioned drawbacks.

SUMMARY OF THE INVENTION

The subject matter of the invention is a composition for releasing an active principle, comprising:
- a porous matrix;
- a carrier loaded with said matrix;
- the active principle in the carrier.

According to one embodiment, the porous matrix is a ceramic matrix, preferably made of alumina $Al_2O_3$.

According to one variation on the foregoing embodiment, the ceramic matrix presents a porosity by volume of 45% to 75%, a pore size of 200 μm to 600 μm, said ceramic being obtained via impregnation of a foam, pre-sintering at a temperature greater than 1200° C., over-impregnation by a slurry, and sintering at a temperature greater than 1600° C.

According to one embodiment, the carrier is a gel.

According to one variation on the foregoing embodiment, the gel is a PLA-PEG-PLA gel.

According to another variation on the foregoing embodiment, the composition is obtainable by impregnating said gel via pressurization.

According to another variation on the foregoing embodiment, the gel is formed in situ and the carrier is a gel precursor.

Such a gel precursor can be a lyophilisate. The composition is obtainable by impregnating the matrix with a liquid then by lyophilisation.

Such a gel precursor can be a polymer solution in an organic solvent. The composition is obtainable by impregnating the matrix with said solution.

According to one embodiment, the active principle is chosen from among growth factors, analgesics, antibiotics and antineoplastics, or a combination of two or several.

According to one embodiment, the active principle is an antibiotic chosen from among the following:
- betalactamines, particularly amoxicillin, oxacillin, cloxacillin, ceftriaxone, cefotaxime, ceftazidime, piperacillin, imipenem, ertapenem, ceftaroline, aztreonam, cefepime, cefazolin;
- fluouroquinolones, particularly ofloxacine, ciprofloxacin, levofloxacin, oxifloxacin;
- aminosides, particularly gentamicin, amikacin;
- glycopeptides, particularly vancomycin, teicoplanin;
- clindamycin;
- clofazimine.

According to one embodiment, the active principle is an antineoplastic chosen from among the following:
- doxorubicin, cisplatin, methotrexate, ifosfamide, cyclophosphamide, vincristine, dactinomycin, etoposide, denosumab.

The subject matter of the invention furthermore is said composition for use thereof as a therapy, particularly in the treatment of bone cancers, particularly bone metastases.

According to one embodiment, said composition is useful as a therapy in the form of blocks of bone filler, blocks for corpectomy, cervical or lumbar spinal interbody cages or spacers, cervical spacers, spacers for the calcaneus, osteotomy spacers such as tibial expansion spacers, derotation spacers such as anterior tibial tuberosity, rehabilitative spacers, valgisation spacers, reconstruction and filling blocks, pins, fixation and arthrodesis pivots and spacers, trepan caps, arthrodesis blocks to maintain the natural gap or intervertebral spacing, special reconstruction implants: sinus filler blocks, orbit floor and roof filler blocks, craniotomy plugs, filler implants and maxillofacial reconstruction plates, and any anatomical part on which it is possible to reinsert "nerves" or "facia lata" tissue.

This composition is advantageously a prosthesis or an implant.

DESCRIPTION OF THE EMBODIMENTS OF THE INVENTION

The invention is now described in more detail and in a non-limiting manner in the following description.

Unless otherwise indicated, the proportions or percentages shown are by weight.

Porous Matrix

Porous matrices suitable for receiving the gel can be used. For example, ceramic (described more in detail hereinafter) or even trabecular metal are such matrices. Said trabecular metal is particularly used by the Zimmer company.

Ceramic

The preferred ceramic matrix of the invention is made from alumina $Al_2O_3$, which is porous in order to allow for it to be loaded with the carrier and the active principle. Said alumina ceramic is known per se but can be used doped with another material such as Zirconia. All other ceramics (for example, hydroxyapatite, zirconia/alumina mixture, zirconia, etc.) can be used.

The porosity (open or interconnected) of said ceramic can particularly be between 40% and 80%, preferably between 60% and 70%, advantageously approximately 65%.

The size of the pores is typically between 200 μm and 600 μm, preferably 400 μm.

The porosity/size of the pores is measured by mercury porosimetry. Porosity is defined by the difference between the volume occupied by the pores over the total volume, the total volume being the sum of the volume of the pores and alumina. The weight of aluminium being defined by the volume and the density, by weighing the sample and identifying the total volume thereof, the volume of the pores and thus the porosity (open) can be determined by the difference.

The size of the ceramic matrix can vary from a few millimetres to many centimetres, even tens of centimetres; the volume can be between 1 and 250 $cm^3$.

Mechanical resistance to compression is advantageously between 20 MPa and 60 MPa, advantageously greater than 40 MPa.

All known methods for preparing porous alumina can generally be used.

Particularly, a method comprising the following steps can be used:
- (A) providing a pore forming material (such as foam, for example, polyurethane foam, allowing particularly the porosity and the size of the pores to be adjusted) and impregnation of the pore forming material with a suspension of ceramic alumina particles (alumina slurry) possibly mixed with various organic additives such as binders, plasticizer and dispersant;
- (B) oven drying;
- (C) heat treatment at a low temperature (less than 700° C.) to eliminate the foam and the organic components of the suspension; then
- (D) sintering at a temperature greater than 1500° C.

The method described in patent application FR2823674 can be used advantageously. Particularly, the ceramic matrix of the invention can be prepared using the method described therein. In the preferred embodiment, after implementing the first two phases as described hereinbefore (phases A and B), the porous ceramic piece is pre-sintered to a temperature greater than 1200° C., which gives same greater cohesiveness (phase C'). The cycle continues with an additional dipping of the piece in another suspension of ceramic particles (phase E). The viscosity of said concentrated suspension is controlled due to several organic additives (binders, plasticizers, dispersants) in order to be adapted to a homogenous impregnation of the pre-sintered porous piece. After another oven drying (phase B') and pyrolysis of the organic additives of the suspension (phase C), the ceramic piece is finally sintered at a temperature greater than 1600° C. following an adapted cycle (phase D').

Said over-impregnation method reinforces the mechanical properties of the intered ceramic and multiplies the resistance thereof by a coefficient of 2, particularly compression breaking stress.

Such a ceramic is available to the applicant, under the brand name Ceramil®.

The desired shape can be given to the matrix either before or after the carrier (and the active principles) are loaded or by machining.

Carrier

The carrier is a composition that will allow the active principle to be retained in the pores of the ceramic. Said carrier is any carrier suitable for being loaded into the pores of the ceramic, and can particularly be in the form of a gel or in the form of a liquid that can be lyophilized. The carrier is used to release the active principle according to a selected release profile.

The ceramic matrix can be loaded with powder as follows: the active suspension in a liquid or gelatinous form is introduced into the ceramic matrix and then lyophilisation is carried out.

The liquid form can be in a lyophilized form after reprocessing. In this liquid form, the carrier can possibly be suitable to be rehydrated once the implant is in place in the human body, the lyophilized liquid form is converted in situ into a salting out principle via rehydration. The carrier is effective in said rehydrated form. In said form, it is possible to combine the two variations, rehydration taking place via contact and blood pressure whereas lyophilisation is carried out after mixing the carrier with the active principle, and after loading same in the matrix.

The gel embodiment is preferred. Any gel suitable as a carrier for an active principle can be used, such as hydrogels, gels made from polylactic acid (PLA) or with a comonomer (PLGA), gels made from diblock or triblock, etc. Suitable gels are described in the following publications: K. Al-Tahami and J. Singh "Smart Polymer Based Delivery Systems for Peptide and Proteins," Recent Patents on Drug Delivery & Formulation, 1: pages: 65-71 Bentham Science Publishers, 2007, U.S. Pat. No. 6592899, U.S. Pat. No. 6541033, U.S. Pat. No. 6350812, WO2012/090070, WO2014001904 and WO2014001905.

A suitable gel is a gel made from diblock or triblock, particularly PLA-PEG-PLA, and/or the gel that is the subject matter of the patent WO2012/090070.

The gel can have a viscosity between 100 Cp and 1400 Cp.

The gel can be loaded in the ceramic matrix via various methods. The rate of final incorporation, defined as being the ratio between the volume of polymer gel loaded and the available porous volume of the ceramic matrix, is generally between 50% and 100%, generally 100%. Said rate of final incorporation is defined as the rate of initial incorporation (the rate after the loading of the gel) multiplied by the rate of retention, said rate of retention being the factor expressing the capacity of the gel to remain in the ceramic matrix. A first method comprises the step of pressurization to constrain the gel intended to penetrate the ceramic matrix. With this method, the rate of incorporation is high, but the rate of retention determined in vitro is approximately 80%. Therefore, the rates of retention measured a 1 hour and 24 hours, under the in vitro experimental conditions, vary from 80-95% to 50-65%. However, once implanted in vivo, the surrounding tissues will prevent the gel from quickly coming out of the matrix, which will allow a high rate of incorporation to be preserved, typically greater than 60%.

A second method comprises the step of forming the gel in situ in the ceramic matrix. In this second method, the polymer is dissolved in an organic solvent, loaded in the matrix then placed into contact with an aqueous solution (typically a buffer).

The kinetics of the releasing of the active principle contained in the gel or the carrier contained in the matrix is adjustable in a manner that is known per se. Indeed, the carriers or gels have profiles or kinetics of the releasing of the active principle that are adjustable. Specific release profiles can be generated and adapted to each patient.

For example, a release profile in the body is such that there is a first salting out peak on the first day and then a decrease on the following 10 to 30 days. Therefore, a continuous salting out can further be predicted.

Active Principle

In general, all active principles can be used in the invention. For example, growth factors, analgesics, antibiotics and antineoplastics/antitumor factors, or a combination of two or several.

The antibiotics can be chosen from among the following:

betalactamines, particularly amoxicillin, oxacillin, cloxacillin, ceftriaxone, cefotaxime, ceftazidime, piperacillin, imipenem, ertapenem, ceftaroline, aztreonam, cefepime, cefazolin;

fluouroquinolones, particularly ofloxacine, ciprofloxacin, levofloxacin, oxifloxacin;

aminosides, particularly gentamicin, amikacin;

glycopeptides, particularly vancomycin, teicoplanin;

clindamycin;

clofazimine.

The antineoplastics can be chosen from the list of known antineoplastics, for example:

osteosarcomas and fusiform bone sarcomas: doxorubicin, cisplatin, methotrexate, ifosfamide;

Ewing sarcomas: doxorubicin, cyclophosphamide, ifosfamide, vincristine, dactinomycin, etoposide;

giant cell tumours: denosumab;

soft tissue sarcomas: doxorubicin.

Uses

The invention lends itself to a large number of uses, particularly in traumatology for fracture reconstructions, in orthopaedics as filler elements, or as implants (spinal vertebrae fusion, etc.), for expansion osteotomies and the reconstructions (for example, maxillofacial) and particularly for surgeries as a treatment for bone cancer, whether primary or secondary. The invention permits the production of a number of bone substitutes and implants, which can be used, for example, as expansion spacers or as a bone filler throughout the skeletal system.

For example, blocks of bone filler, blocks for corpectomy, cervical or lumbar spinal interbody cages or spacers, cervical spacers, spacers for the calcaneus, osteotomy spacers (e.g. tibial expansion spacers), derotation spacers (e.g. anterior tibial tuberosity), rehabilitative spacers, valgisation spacers, reconstruction and filling blocks, pins, fixation and arthrodesis pivots and spacers, trepan caps, arthrodesis blocks to maintain the natural gap or intervertebral spacing, special reconstruction implants: sinus filler blocks, orbit floor and roof filler blocks, craniotomy plugs, bone filler implants regardless of where in the skeletal system same are implanted, and, in a general way, any anatomical part on which it is possible to reinsert "nerves" or "facia lata" tissue regardless of where in the skeletal system same are implanted.

The following examples illustrate the invention without limiting it.

Example 1

The ceramic alumina is a Ceramil® ceramic. Tests on 4 samples indicate good homogeneity in the porosity of the different spacers (52±2%) which are impregnated with polymer solutions. The matrix is a cylindrical shape.

The gel is a PLA-PEG-PLA triblock gel.

Same can be loaded into the matrix by pressurization or be formed in situ in the matrix.

According to the first loading method, the gel is introduced via pressurization in the ceramic matrix.

The method was tested with two hydrogels, hard and soft respectively. These two gels are the following (the DMSO is the organic solvent, whereas the aqueous phase is the PBS buffer):

| Hydrogel | Polymer | DMSO | PBS |
|----------|---------|------|-----|
| Soft     | 24      | 16   | 60  |
| Hard     | 42      | 18   | 40  |

The two gels can be loaded with problems by pressurization.

Clofazimine is a coloured and highly hydrophobic antibiotic. This molecule is incorporated in the hydrogels and remains strongly associated therewith due to its being highly hydrophobic. Clofazimine can therefore be used as a hydrogel "marker". 5 hydrogels are now prepared.

The gels were formulated by the so-called "push-pull" method which consists of quickly mixing the contents of 2 mutually connected syringes—one of the syringes containing a PLA-PEG-PLA trisequenced polymer solution dissolved in a biocompatible solvent and the other containing an aqueous phase.

The polymer used for this study has a molar mass of 14 kD, the biocompatible solvent is dimethyl sulfoxide (DMSO) and the aqueous phase is a phosphate buffer (PBS).

By modifying the concentration of the polymer in the solvent contained in one of the syringes and the proportion of said solution and the aqueous phase, it is possible to obtain gels with different compositions. As a general rule, the greater the proportion of the polymer, the more important the consistency thereof. The following table indicates the composition of the hydrogels used in this study.

| Hydrogel | Polymer | DMSO | PBS |
|----------|---------|------|-----|
| 1.1      | 24      | 16   | 60  |
| 1.2      | 30      | 20   | 50  |
| 1.3      | 35      | 15   | 50  |
| 1.4      | 42      | 18   | 40  |
| 1.5      | 50      | 20   | 30  |

The clofazimine is dissolved in a polymer solution with a concentration of 1% before the mixing (push-pull) of the contents of the 2 syringes is carried out. The gels thus obtained are strongly coloured red-maroon.

The gels of increasing hardness are incorporated by pressure using a press. All the gels penetrated the spacer matrices without difficulty except for the hardest gel. In this latter case, the pressure used on the pusher led to the breakage of the glass tube containing the matrix; the replacement glass tube allows the gel to be loaded.

The rate of incorporation of the gel in the ceramic spacer is determined, which is defined as the ratio between the volume of incorporated gel and the volume of the pores. The incorporation rate does not vary substantially on the basis of the nature of the gel.

| Hydrogel | Incorporation rate |
|----------|--------------------|
| 1.1      | 82                 |
| 1.2      | 82                 |
| 1.3      | 82                 |
| 1.4      | 85                 |

The ceramic matrices are placed in 15 ml Falcon tubes containing 5 ml of PBS. After 1 hour, hydrogel is observed coming out of the external pores of the matrix. The incubation media at t=1 hour are then replaced with 5 ml of PBS buffer. After 24 hours, the hydrogel is likewise observed to be coming out. The matrices are lightly scraped with a spatula to remove the gel on the surface thereof and the incubation media are removed. The gel on the incubation media is recovered by centrifugation at 3000 g at the ambient temperature for 20 min (Jouan CR422 centrifuge). The clofazimine in the gel is then dosed.

| Hydrogel | Rate of retention 1 hour | Rate of retention 24 hours |
| --- | --- | --- |
| 1.1 | 85 | 63 |
| 1.2 | 83 | 53 |
| 1.3 | 83 | 52 |
| 1.4 | 94 | 59 |
| 1.5 | 92 | 60 |

Hydrogels tend to come out of the matrix throughout the study (24 hours). However, the retention remains acceptable since it is approximately 85% and 55% at 1 hour and 24 hours respectively.

In order to obtain a ceramic matrix filled with gel, another method consisting of forming the gel directly in the ceramic. The spacer matrices must be impregnated first with an organic polymer solution. The incubation of the matrices in an aqueous medium leads then to the formation of the gel in the ceramic (in situ formation).

This second method was tested with 5 polymer solutions.

The organic solutions are prepared by dissolving a PLA-PEG-PLA trisequenced copolymer with a molar mass of 36 kd) into N-methyl pyrolidone (NMP) at 50° C. for 5 hours.

The tests are carried out with solutions of different concentrations: 30%, 40%, 50%, 60% and 70% (wt/wt), 2.1 to 2.5. The clofazamine is incorporated in the solutions at a final concentration of 1% (wt/wt).

In order to cause the organic solutions to penetrate into the matrices using pressure, pressure manually put on the pusher is sufficient. The 30% and 40% solutions are even capable of passively impregnating the gel in approximately 5 minutes with no pressure needing to be applied. There is therefore no difficulty in incorporating the polymer solutions into the matrices. However, the most diluted organic solutions tend to diffuse out of the ceramic once said ceramic is removed from the pressurization device, since the viscosity thereof is insufficient to maintain the polymer solution in the ceramic.

| Precursor | Rate of incorporation |
| --- | --- |
| 2.1 | 57 |
| 2.2 | 59 |
| 3.3 | 68 |
| 3.4 | 72 |
| 4.5 | 82 |

The rate of incorporation is between 57% and 82%, the weakest rate being obtained with the least viscous solution, and the highest rate with the most viscous solution. This is largely due to the fact that the low-viscosity solutions diffuse out of the matrix once the matrix is removed from the pressurization device.

Then, incubation is carried out in PBS as per the aforementioned. The results are as follows:

| Hydrogel | Rate of retention 1 hour | Rate of retention 24 hours |
| --- | --- | --- |
| 2.1 | 99 | 99 |
| 2.2 | 100 | 100 |
| 2.3 | 100 | 100 |
| 2.4 | 100 | 100 |
| 2.5 | 100 | 100 |

With the least viscous solution, a quantity equivalent to approximately 1% of the initial dose was detected in the incubation medium. In the other media, the detected quantities were less than 0.2%.

The formation of gel in situ in the ceramic leads to a rate of retention that is nearly 100% in a 24-hour period.

Loading the ceramic matrix with an organic polymer solution as a gel precursor at an adapted viscosity (high and thus a high content of polymer in the organic solution) and implanting the matrix into the patient can thus be envisaged, with the body's aqueous fluids surrounding the matrix thus leading to the formation of the gel. There is therefore a second option in addition to kinetics for releasing the active principle into the patient.

The invention claimed is:

1. A prosthesis or an implant adapted for the release of an active principle in a human body, comprising:
   a sintered, porous ceramic matrix made from alumina, in which a pore size is between 200 µm and 600 µm;
   a carrier impregnated in pores of said sintered, porous ceramic matrix, the carrier being a lyophilizate which is obtained by impregnating the sintered, porous ceramic matrix with a liquid and then lyophilizing; and
   the active principle in the carrier;
   wherein:
   lyophilization is carried out after mixing the carrier with the active principle, and after loading same in the matrix,
   the mix of carrier and active principle is rehydrated once the implant is in place in the human body, the lyophilized liquid form being converted in situ into a salting out principle via rehydration,
   the active principle is an antibiotic,
   the sintered, porous ceramic matrix has a volume of between 1 and 250 cm$^3$,
   the prosthesis or implant is adapted for use as a therapy as blocks of bone filler, blocks for corpectomy, cervical or lumbar spinal interbody cages or spacers, cervical spacers, spacers for calcaneus, osteotomy spacers, derotation spacers, rehabilitative spacers, valgisation spacers, reconstruction and filling blocks, pins, fixation and arthrodesis pivots and spacers, trepan caps, arthrodesis blocks to maintain a natural gap or intervertebral spacing, craniotomy plugs, filler implants and maxillofacial reconstruction plates, or an anatomical part on which it is possible to insert "nerves" or "facia lata" tissue, and
   the prosthesis or implant has a mechanical resistance to compression of between 20 MPa and 60 MPa.

2. The prosthesis or implant according to claim 1, in which the porosity of the sintered, porous ceramic matrix is between 40% and 80%.

3. The prosthesis or implant according to claim 1, in which the sintered, porous ceramic matrix presents a porosity by volume of 45% to 75%, the ceramic being obtained by impregnation of a foam, pre-sintering at a temperature greater than 1200° C., over-impregnation by a slurry, and sintering at a temperature greater than 1600° C.

4. The prosthesis or implant of claim 1, in which the active principle is an antibiotic chosen from the group consisting of:
   Betalactamines;
   Fluoroquinolones;
   Glycopeptides;
   Aminosides;
   Clindamycin; and
   Clofazimine.

5. The prosthesis or implant of claim 1, wherein the carrier does not include a gel.

6. The prosthesis or implant according to claim 1, wherein a release profile of the active principle in the human body is such that there is a first salting out peak on the first day.

\* \* \* \* \*